US008508100B2

(12) United States Patent
Lee et al.

(10) Patent No.: US 8,508,100 B2
(45) Date of Patent: Aug. 13, 2013

(54) SURFACE ACOUSTIC WAVE ELEMENT, SURFACE ACOUSTIC WAVE DEVICE AND METHODS FOR MANUFACTURING THE SAME

(75) Inventors: Hun Joo Lee, Seoul (KR); Soosuk Lee, Seoul (KR); Chinsung Park, Yongin-si (KR); Kieun Kim, Seoul (KR)

(73) Assignee: Samsung Electronics Co., Ltd. (KR)

( * ) Notice: Subject to any disclaimer, the term of this patent is extended or adjusted under 35 U.S.C. 154(b) by 2 days.

(21) Appl. No.: 12/542,983

(22) Filed: Aug. 18, 2009

(65) Prior Publication Data

US 2010/0109475 A1 May 6, 2010

(30) Foreign Application Priority Data

Nov. 4, 2008 (KR) .................. 10-2008-0109042
Dec. 29, 2008 (KR) .................. 10-2008-0135542

(51) Int. Cl.
*H01L 41/08* (2006.01)

(52) U.S. Cl.
USPC .................................. 310/313 R; 310/313 A (58) Field of Classification Search
USPC .............. 310/313 A, 313 R, 313 D, 363, 364, 310/321
See application file for complete search history.

(56) References Cited

U.S. PATENT DOCUMENTS

| | | | |
|---|---|---|---|
| 4,472,652 A * | 9/1984 | Brice et al. .................. | 310/313 B |
| 4,598,224 A * | 7/1986 | Ballato ..................... | 310/313 R |
| 5,051,645 A * | 9/1991 | Brace et al. ................ | 310/313 D |
| 5,216,312 A * | 6/1993 | Baer et al. .................. | 310/313 D |
| 5,221,871 A * | 6/1993 | Fuchs et al. ................ | 310/313 R |
| 5,283,037 A * | 2/1994 | Baer et al. .................... | 422/82.01 |
| 5,447,845 A * | 9/1995 | Chu et al. .................... | 435/6.11 |
| 6,075,307 A * | 6/2000 | Fukiharu ................... | 310/313 R |
| 6,379,969 B1 | 4/2002 | Mauze et al. | |
| 6,621,192 B2 * | 9/2003 | Lu et al. .................... | 310/313 A |
| 6,680,206 B1 | 1/2004 | McDevitt et al. | |
| 7,122,938 B2 * | 10/2006 | Noguchi et al. .......... | 310/313 A |
| 7,413,892 B2 * | 8/2008 | Hunt .......................... | 435/287.2 |
| 7,564,174 B2 * | 7/2009 | Matsuda et al. ............. | 310/346 |
| 7,659,653 B2 * | 2/2010 | Matsuda et al. .......... | 310/313 B |
| 7,919,909 B2 * | 4/2011 | Sabah et al. .................. | 310/348 |
| 7,944,125 B2 * | 5/2011 | Takada et al. ................ | 310/348 |
| 8,217,551 B2 * | 7/2012 | Matsuo ..................... | 310/313 R |
| 2003/0233864 A1 | 12/2003 | Rodier | |

(Continued)

FOREIGN PATENT DOCUMENTS

| | | |
|---|---|---|
| JP | 2001085969 | 3/2001 |
| JP | 2005072942 | 3/2005 |

(Continued)

OTHER PUBLICATIONS

R.C. Furneaux, G.E. Thompson & G.C. Wood; The Application of Ultramicrotomy to the Electronoptical Examination of Surface Films on Aluminium; Corrosion Science, vol. 18, pp. 853-881; Pergamon Press Ltd. 1978, Printed in Great Britain.

*Primary Examiner* — Mark Budd
(74) *Attorney, Agent, or Firm* — Cantor Colburn LLP (57) ABSTRACT

A surface acoustic wave ("SAW") element includes a substrate which is formed of a piezoelectric material, a plurality of first electrodes which are disposed on the substrate and separated from each other, a plurality of second electrodes which are disposed on the substrate and are separated from the first electrodes and are separated from each other, and oxide films which are disposed on the respective plurality of first electrodes and the plurality of second electrodes.

30 Claims, 9 Drawing Sheets

(56) References Cited

U.S. PATENT DOCUMENTS

| | | |
|---|---|---|
| 2005/0116263 A1 | 6/2005 | Lu et al. |
| 2006/0033039 A1 | 2/2006 | Williams et al. |
| 2007/0145862 A1 | 6/2007 | Kimura et al. |
| 2007/0154349 A1 | 7/2007 | Kimura et al. |

FOREIGN PATENT DOCUMENTS

| | | |
|---|---|---|
| KR | 1020040004713 | 1/2004 |
| KR | 1020050024783 A | 3/2005 |
| KR | 1020060085251 | 7/2006 |

* cited by examiner

SURFACE ACOUSTIC WAVE ELEMENT, SURFACE ACOUSTIC WAVE DEVICE AND METHODS FOR MANUFACTURING THE SAME

CROSS-REFERENCE TO RELATED APPLICATIONS

This application claims priority to Korean Patent Application No. 10-2008-0109042 filed on Nov. 4, 2008 and Korean Patent Application No. 10-2008-0135542 filed on Dec. 29, 2008, and all the benefits accruing therefrom under 35 U.S.C. §119, the contents of which in their entireties are herein incorporated by reference.

BACKGROUND

1) Field

The general inventive concept relates to a surface acoustic wave ("SAW") element, a SAW device and methods for manufacturing the same.

2) Description of the Related Art

A SAW sensor is, in general, a device that detects a target material in a sample using a piezoelectric material. An oscillation signal is applied to the SAW sensor. Using an interdigital transducer ("IDT") electrode included in the SAW sensor, the oscillation signal is converted into a SAW, which is a mechanical wave, and vice versa.

When the target material in the sample is bound to the surface of the SAW sensor, a surface mass of the SAW sensor may change due to the material bound to the surface. The target material being bound to the surface of the SAW sensor may cause a change in a SAW which is generated by the IDT electrode.

Further, when the target material is a biological material, the sample may include salt. A leakage current may undesirably flow through the sample having the salt from the portions of the SAW where electrical signals are input to the SAW sensor or output from the SAW sensor. When the leakage current occurs, a wave for oscillation or resonance is not be generated in the SAW sensor, resulting in the SAW sensor not being able to accurately sense the target material.

SUMMARY

Exemplary embodiments provide a surface acoustic wave element, a surface acoustic wave device and methods for manufacturing the same, capable of effectively preventing leakage current from occurring when either applying electrical signals to the surface acoustic wave element or detecting electrical signals from the surface acoustic wave element.

In one exemplary embodiment, a surface acoustic wave element includes a substrate which is disposed of piezoelectric material; a plurality of first electrodes which are disposed on the substrate and are separated from each other; a plurality of second electrodes which are disposed on the substrate and are separated from the first electrodes and are separated from each other; and oxide films which are disposed on the respective plurality of first electrodes and plurality of second electrodes.

In one exemplary embodiment, each of the plurality of first electrodes and the plurality of second electrodes comprises a surface-oxidizable conductive material.

In one exemplary embodiment, the surface-oxidizable conductive material is at least one of a metal and an alloy.

In one exemplary embodiment, the surface-oxidizable conductive material comprises at least one of aluminum, niobium, tantalum, titanium, tungsten, zirconium, copper and chromium.

In one exemplary embodiment, each of the plurality of first electrodes and the plurality of second electrodes is an interdigital transducer electrode.

In another exemplary embodiment, a method for manufacturing a surface acoustic wave element includes providing a substrate which is a piezoelectric material, a plurality of first electrodes which are disposed on the substrate and are separated from each other and a plurality of second electrodes which are disposed on the substrate and are separated from the plurality of first electrodes and are separated from each other; and disposing oxide films on the respective plurality of first electrodes and plurality of second electrodes.

In one exemplary embodiment, disposing the oxide films comprises dry oxidizing the plurality of first electrodes and the plurality of second electrodes.

In one exemplary embodiment, disposing the oxide films comprises exposing the plurality of first electrodes and the plurality of second electrodes to at least one of a plasma and ozone.

In one exemplary embodiment, disposing the oxide films comprises thermally oxidizing the plurality of first electrodes and the plurality of second electrodes.

In one exemplary embodiment, disposing the oxide films comprises wet oxidizing the plurality of first electrodes and the plurality of second electrodes.

In one exemplary embodiment, disposing the oxide films comprises anodizing the plurality of first electrodes and the plurality of second electrodes.

In one exemplary embodiment, disposing the oxide films comprises exposing the plurality of first electrodes and the plurality of second electrodes to at least one of hydrogen peroxide, sodium bicarbonate, lead dioxide, manganese dioxide, potassium permanganate, sodium hypochlorite and chlorine oxide.

In another exemplary embodiment, a surface acoustic wave device includes a surface acoustic wave element having a first pad portion; a first substrate having a second pad portion; a connecting portion which electrically connects the first pad portion and the second pad portion; and an oxide film which is disposed on the first pad portion, the second pad portion and the connecting portion.

In one exemplary embodiment, each of the first pad portion, the second pad portion and the connecting portion comprises a surface-oxidizable conductive material.

In one exemplary embodiment, the connecting portion has a shape of at least one of a line, a curved figure and a polyhedron.

In one exemplary embodiment, a surface acoustic wave element further includes a second substrate which is a piezoelectric material; a plurality of first electrodes which are disposed on the second substrate and areas separated from each other; a plurality of second electrodes which are disposed on the second substrate and are separated from the first electrodes and are separated from each other; and oxide films which are disposed on the respective plurality of first electrodes and plurality of second electrodes, wherein the first pad portion is constructed integrally with the plurality of first electrodes and the plurality of second electrodes.

In another exemplary embodiment, a method for manufacturing a surface acoustic wave device includes providing a surface acoustic wave element having a first pad portion and a substrate having a second pad portion; electrically connecting the first pad portion and the second pad portion using a connecting portion; and disposing an oxide film on the first pad portion, the second pad portion and the connecting portion.

In one exemplary embodiment, disposing the oxide film comprises dry oxidizing the first pad portion, the second connection and the connecting portion.

In one exemplary embodiment, disposing the oxide film comprises exposing the first pad portion, the second pad portion and the connecting portion to at least one of a plasma and ozone.

In one exemplary embodiment, disposing the oxide film comprises thermally oxidizing the first pad portion, the second pad portion and the connecting portion.

In one exemplary embodiment, disposing the oxide film comprises wet oxidizing the first pad portion, the second pad portion and the connecting portion.

In one exemplary embodiment, disposing the oxide film comprises anodizing the first pad portion, the second pad portion and the connecting portion.

In one exemplary embodiment, disposing the oxide film comprises exposing the first pad portion, the second pad portion and the connecting portion to at least one of hydrogen peroxide, sodium bicarbonate, lead dioxide, manganese dioxide, potassium permanganate, sodium hypochlorite and chlorine oxide.

In another exemplary embodiment, a surface acoustic wave element includes a substrate which is constructed of a piezoelectric material; first and second interdigital transducers which are disposed on the substrate, the first interdigital transducer having a first plurality of electrodes and the second interdigital transducer having a second plurality of electrodes; first and second oxide films which are disposed on the first and second plurality of electrodes, respectively; a sensing area which is disposed on the substrate which bonds to a target material, such that the first plurality of electrodes generate a surface acoustic wave on the substrate in response to a first electrical signal and the second plurality of electrodes generate a second electrical signal in response to receiving the surface acoustic wave, the second electrical signal being indicative of an amount of the target material bonded to the sensing area.

In one exemplary embodiment, the target material communicating with the sensing area is disposed in a liquid and the first and second oxide films prevent a leakage current from flowing from the first plurality of electrodes and the second plurality of electrodes, respectively, to the liquid.

In one exemplary embodiment, the surface acoustic wave element further includes a first metal pad disposed on the substrate and directly coupled to the first plurality of electrodes, the first oxide film being further disposed on the first metal pad.

In one exemplary embodiment, the surface acoustic wave element further includes a second metal pad disposed on the substrate and a metal wire coupling the second metal pad to the first metal pad, the first oxide film being further disposed on the second metal pad and the metal wire.

In another exemplary embodiment, a method for manufacturing a surface acoustic wave device includes disposing first and second interdigital transducers on a substrate, the substrate being constructed of a piezoelectric material, the first interdigital transducer having a first plurality of electrodes and the second interdigital transducer having a second plurality of electrodes; disposing a first oxide film on the first plurality of electrodes; and disposing a second oxide film on the second plurality of electrodes.

In one exemplary embodiment, the method for manufacturing the surface acoustic wave device further includes disposing a first metal pad on the substrate that is directly coupled to the first plurality of electrodes, wherein the first oxide film is further disposed on first metal pad.

In one exemplary embodiment, the method for manufacturing the surface acoustic wave device further includes disposing a second metal pad on the substrate; and coupling a metal wire to both the first and second metal pads, wherein the first oxide film is further disposed on the second metal pad and the metal wire.

In another exemplary embodiment, a surface acoustic wave device includes a substrate which is constructed of a piezoelectric material; a first surface acoustic wave element having first and second interdigital transducers, first and second oxide films and a sensing area, the first interdigital transducer being disposed on the substrate and having a first plurality of electrodes; the second interdigital transducer being disposed on the substrate and having a second plurality of electrodes, the first and second oxide films being disposed on the first and second plurality of electrodes, respectively, the sensing area being disposed on the substrate and bonds to a target material; a second surface acoustic wave element having third and fourth interdigital transducers and third and fourth oxide films and no sensing area, the third interdigital transducer being disposed on the substrate and having a third plurality of electrodes, the fourth interdigital transducer being disposed on the substrate and having a fourth plurality of electrodes, the third and fourth oxide films being disposed on the third and fourth plurality of electrodes, respectively; such that the first plurality of electrodes generate a first surface acoustic wave on the substrate in response to a first electrical signal and the second plurality of electrodes generate a second electrical signal in response to receiving the first surface acoustic wave; and such that the third plurality of electrodes generate a second surface acoustic wave on the substrate in response to a third electrical signal and the fourth plurality of electrodes generate a fourth electrical signal in response to receiving the second surface acoustic wave, wherein a difference between a first parameter of the second electrical signal and a second parameter of the fourth electrical signal is indicative of an amount of the target material bonded to the sensing area.

In one exemplary embodiment, the target material communicating with the sensing area is disposed in a liquid and the first and second oxide films prevent a leakage current from flowing from the first plurality of electrodes and the second plurality of electrodes, respectively, to the liquid.

BRIEF DESCRIPTION OF THE DRAWINGS

The above and other aspects, advantages and features of exemplary embodiments will become more apparent by describing in further detail exemplary embodiments thereof, with reference to the accompanying drawings, in which.

DETAILED DESCRIPTION

Exemplary embodiments now will be described more fully hereinafter with reference to the accompanying drawings. Exemplary embodiments may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross-sectional illustrations that are schematic illustrations of exemplary embodiments. As such, variations from the shapes of the illustrations as a result, for example, of manufacturing techniques and/or tolerances, are to be expected. Thus, exemplary embodiments should not be construed as limited to the particular shapes of regions illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present specification.

Hereinafter, exemplary embodiments will be described in detail with reference to the accompanying following drawings.

Figure 1:
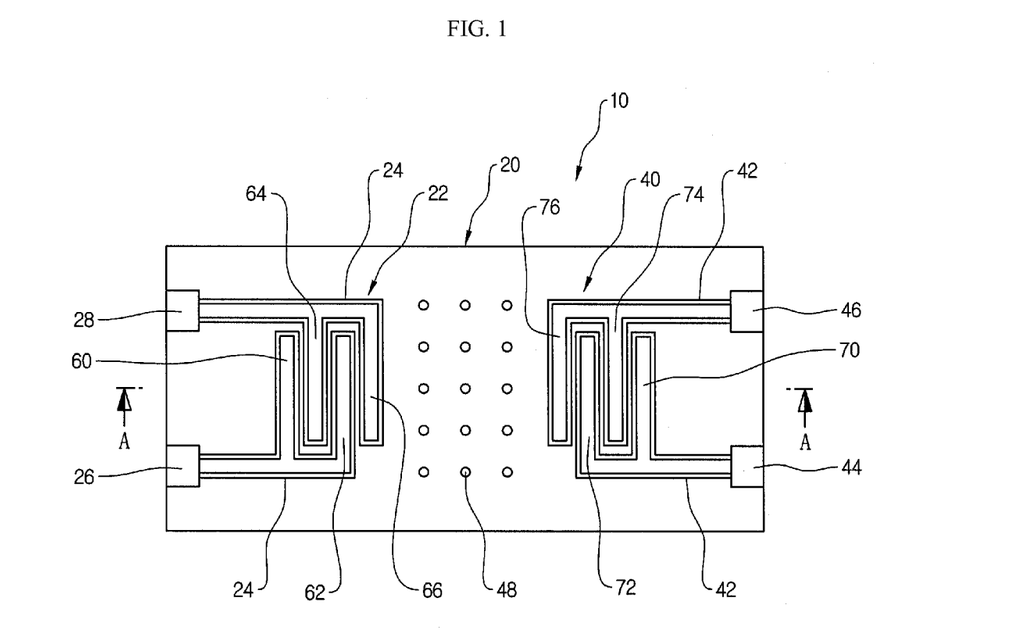
FIG. 1 is a top plan view illustrating an exemplary embodiment of a surface acoustic wave ("SAW") element.
Figure 2:
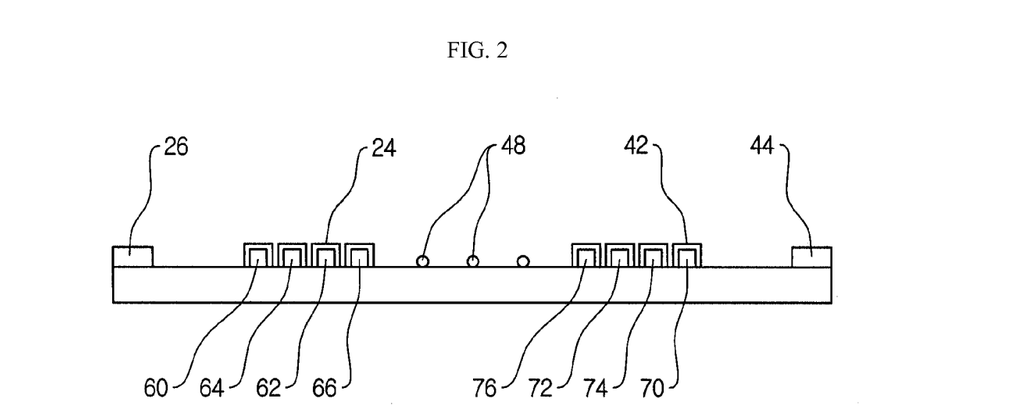
FIG. 2 is a cross-sectional view taken along line A-A' of FIG. 1.

FIG. 1 is a top plan view illustrating an exemplary embodiment of a surface acoustic wave ("SAW") element 10, and FIG. 2 is a cross-sectional view taken along line A-A' of FIG. 1.

Referring to FIG. 1 and FIG. 2, the SAW element 10 may include a substrate 20, an interdigital transducer ("IDT") 22, an oxide film 24, an IDT 40, an oxide film 42, pad portions 44, 46 and receptors 48. The substrate 20 may be formed of a piezoelectric material suitable for generating and propagating a SAW. For example, the substrate 20 may be formed of a single crystal piezoelectric material such as lithium tantalate and lithium niobate, a piezoelectric ceramic such as lead zirconate titanate ("PZT"), or other suitable material.

The IDT 22 having a plurality of first electrodes may be disposed on the substrate 20. Further, the plurality of first electrodes may be spaced apart from each other. For example, the IDT 22 may include the electrodes 60, 62, 64, 66 which are disposed on the substrate 20 and are spaced apart from each other and face each other. When an oscillation signal is applied between the electrodes 60, 62, 64, 66, a SAW, which is a mechanical wave, may be generated at a contact portion of the electrodes 60, 62, 64, 66 and the substrate 20. The SAW may propagate along the surface of the substrate 20.

The IDT 40 having a plurality of second electrodes may be disposed on the substrate 20 and may be spaced apart from the IDT 22. Further, the plurality of second electrodes may be spaced apart from each other. For example, the IDT 40 may include the electrodes 70, 72, 74, 76 which are spaced apart from each other and face each other. When a SAW propagates along the substrate 20 and is transferred to the electrodes 70, 72, 74, 76, the SAW may be converted to an electrical signal at a contact portion of the substrate 20 formed of a piezoelectric material and the electrodes 70, 72, 74, 76.

The electrodes 60, 62, 64, 66 may be an IDT electrodes having a comb-shaped structure. Further, the electrodes 70, 72, 74, 76 may be IDT electrodes having a comb-shaped structure.

The electrodes 60, 62, 64, 66 and the electrodes 70, 72, 74, 76 may be constructed of an electrically conducting material.

Further, the electrodes 60, 62, 64, 66 and the electrodes 70, 72, 74, 76 may be formed of a surface-oxidizable material. Further, the electrodes 60, 62, 64, 66 and the electrodes 70, 72, 74, 76 may be formed of a metal or an alloy. For example, the electrodes 60, 62, 64, 66 and the electrodes 70, 72, 74, 76 may be formed of any metal such as aluminum (Al), niobium (Nb), tantalum (Ta), titanium (Ti), tungsten (W), zirconium (Zr), copper (Cu), chromium (Cr), etc. or alloys thereof, and may be formed of one or more of the metals.

The oxide film 24 may be formed on the electrodes 60, 62, 64, 66 and the oxide film 42 may be formed on the electrodes 70, 72, 74, 76. The electrodes 60, 62, 64, 66 may include pad portions 26, 28 for electrical connection to external devices. The electrodes 70, 72, 74, 76 may also include pad portions 44, 46 for electrical connection to external devices. The pad portions 26, 28 may be connected to an external signal generator such that the pad portions 26, 28 receives an oscillatory electrical signal from the external signal generator. The pad portions 44, 46 may be connected to an external amplifier for amplifying an output signal from the IDT 40. The pad portions 26, 28 may be formed integrally as a part of the electrodes 60, 62, 64, 66 using the same material of the electrodes 60, 62, 64, 66. Further, the pad portions 44, 46 may be formed integrally as part of the electrodes 70, 72, 74, 76 using the same material of the electrodes 70, 72, 74, 76. For electrical connection, the pad portions 26, 28 and the pad portions 44, 46 may be exposed. Therefore, the oxide film 24 may be formed on the electrodes 60, 62, 64, 66 excluding the area of the pad portions 26, 28. Further, the oxide film 42 may be formed on the electrodes 70, 72, 74, 76 excluding the area of the pad portions 44, 46.

The receptors 48 may be disposed on an exposed portion of the substrate 20. The receptors 48 may be constructed of a material which specifically reacts with a target material included in a sample. When the receptors 48 on the substrate 20 are exposed to a sample, a target material included in the sample may specifically bind to the receptors 48. The material utilized to construct the receptors 48 may vary depending on the type of target material. For example, each of the receptors 48 may be a protein, an antibody, DNA, RNA, a cell, an aptamer, a polymer, or the like, but is not limited thereto.

When the target material binds to the receptors 48 on the substrate 20, surface mass, viscosity, density, conductivity, or the like of the SAW element 10 may be changed. Accordingly, a characteristic of the SAW generated by the electrodes 60, 62, 64, 66 may also be changed. As such, by comparing an output signal of the SAW element 10 having the target material bound thereto with an output signal of a reference SAW element with no target material bound thereto, it is possible to analyze the target material quantitatively and qualitatively.

In an exemplary embodiment, the electrodes 60, 62, 64, 66 may be electrically insulated by the oxide film 24 formed on the electrodes 60, 62, 64, 66. Further, the electrodes 70, 72, 74, 76 may be electrically insulated by the oxide film 42 formed on the electrodes 70, 72, 74, 76. As a result, it is possible to prevent the occurrence of a leakage current through the sample even when the SAW element 10 is exposed to a conductive sample. Further, since the oxide film 24 is formed only on the electrodes 60, 62, 64, 66 and the oxide film 42 is formed only on the electrodes 70, 72, 74, 76, it is not necessary to form an additional insulation film on an entire surface of the SAW element 10. Accordingly, a problem of noise generation at an interface of an insulation film may be solved.

In an exemplary embodiment of a method for manufacturing a SAW element, the SAW element 10 may be manufactured by providing the substrate 20, the interdigital transducer 22 having the electrodes 60, 62, 64, 66 and the interdigital transducer 40 having the electrodes 70, 72, 74, 76, and then forming the oxide film 24 on the electrodes 60, 62, 64, 66 and forming the oxide film 42 on the electrodes 70, 72, 74, 76.

In an exemplary embodiment, the oxide film 24 may be formed on the electrodes 60, 62, 64, 66 and the oxide film 42 may be formed on the electrodes 70, 72, 74, 76 by dry oxidation. For example, the oxide film 24 may be formed by exposing the electrodes 60, 62, 64, 66 to a plasma. In particular, oxygen (O2) plasma may be utilized to form the oxide films 24, 42. Alternatively, the oxide film 24 may be formed on the electrodes 60, 62, 64, 66 and the oxide film 42 may be formed on the electrodes 70, 72, 74, 76 by thermally oxidizing the electrodes, or via an ozone cleaning process in which the electrodes are exposed to ozone (O3).

In another exemplary embodiment, the oxide film 24 may be formed on the electrodes 60, 62, 64, 66, and the oxide film 42 may be formed on the electrodes 70, 72, 74, 76 by wet oxidation. For example, the oxide film 24 may be formed on the electrodes 60, 62, 64, 66, and the oxide film 42 may be formed on the electrodes 70, 72, 74, 76 by exposing the electrodes to hydrogen peroxide ("H2O2"). Alternatively, the oxide film 24 may be formed on the electrodes 60, 62, 64, 66 12, 13, and the oxide film 42 may be formed on the electrodes 70, 72, 74, 76 by exposing the electrodes to an oxidizing agent such as sodium bicarbonate ("NaHCO3"), lead dioxide ("PbO2"), manganese dioxide ("MnO2"), potassium permanganate ("KMnO4"), sodium hypochlorite ("NaClO"), chlorine oxide ("Cl2O"), or the like.

Alternatively, the oxide film 24 may be formed on the electrodes 60, 62, 64, 66, and the oxide film may be formed on the electrodes 70, 72, 74, 76 by anodizing the electrodes. As used herein, anodizing may refer to a process whereby electrolysis is performed in an electrolyte solution using a material on which the oxide film will be formed as an anode. As the electrodes 60, 62, 64, 66 and the electrodes 70, 72, 74, 76 are anodized, the material constituting the electrodes may be dissolved into the electrolyte solution while, at the same time, the oxide film 24 may be formed on the electrodes 60, 62, 64, 66, and the oxide film 42 may be formed on the electrodes 70, 72, 74, 76.

For example, the oxide film 24 may be formed on the electrodes 60, 62, 64, 66, and the oxide film 42 may be formed on the electrodes 70, 72, 74, 76 by applying a voltage of about 100 Volts for about 40 minutes in an aqueous solution of ammonium adipate at a temperature of about 70° C. having a concentration of about 150 g/L. The electrolyte solution may contain sulfuric acid ("H2SO4"), oxalic acid ["(COOH)2"], chromic acid, boric acid, borax, ammonium phosphate or ammonium tartrate.

Figure 3A:
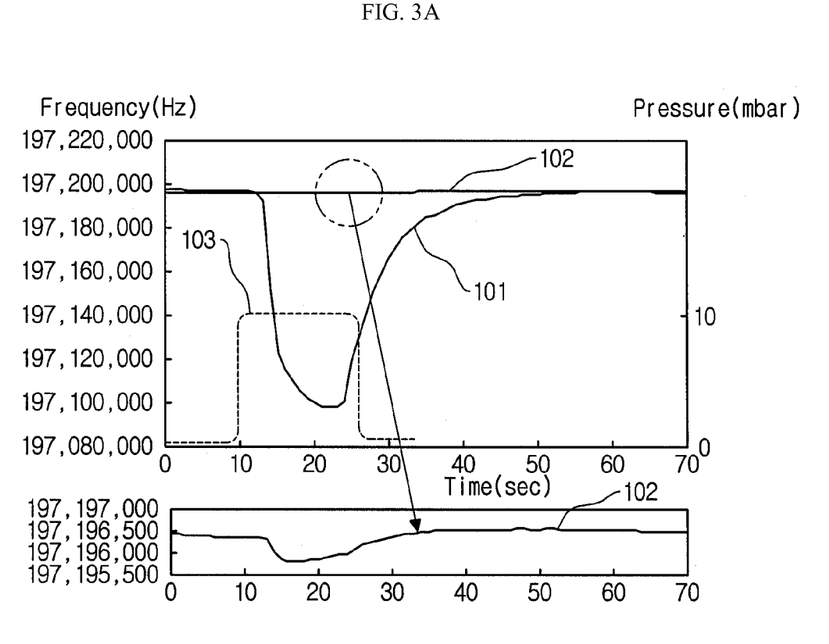
FIGS. 3A-3D are graphs of frequency, pressure and conductivity versus time comparing frequencies of an exemplary embodiment of a SAW element with frequencies of a conventional SAW element.

FIG. 3A is a graph of frequency, in Hertz (Hz), and pressure, in millibars (mbar) versus time, in seconds (sec), which illustrates a frequency of an output signal of an exemplary embodiment of a SAW element and the frequency of an output signal of a SAW element according to the related art as pressure on the sample is changed. As shown, a change of a frequency of the output signal 101 of the exemplary embodiment of the SAW element is relatively larger than a change of a frequency of the output signal 102 of the SAW element according to the related art. The signal 103 indicates a pressure level of a liquid having the sample communicating with the exemplary embodiment of the SAW element over time.

Figure 3B:
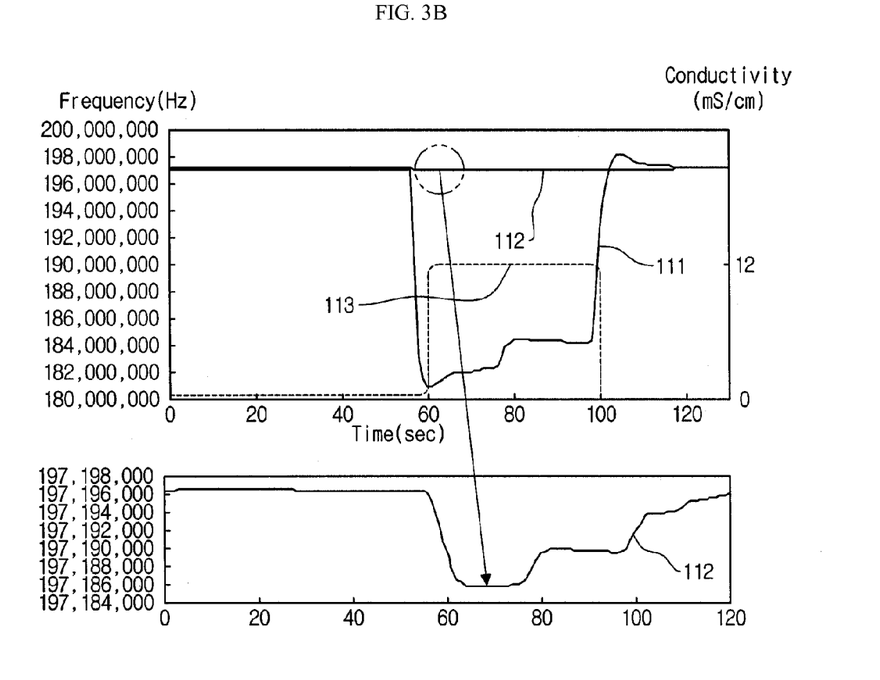

FIG. 3B is a graph of frequency, in Hz, and conductivity, in milliSiemens per centimeter (mS/cm), versus time, in sec, which illustrates a frequency of an output signal of an exemplary embodiment of a SAW element and a frequency of an output signal of a SAW element according to the related art as conductivity of the sample is changed. As shown, a change of a frequency of the output signal 111 of the exemplary embodiment of the SAW element is relatively larger than a change of a frequency of the output signal 112 of the SAW element according to the related art. The signal 113 indicates the conductivity of the sample over time.

Figure 3C:
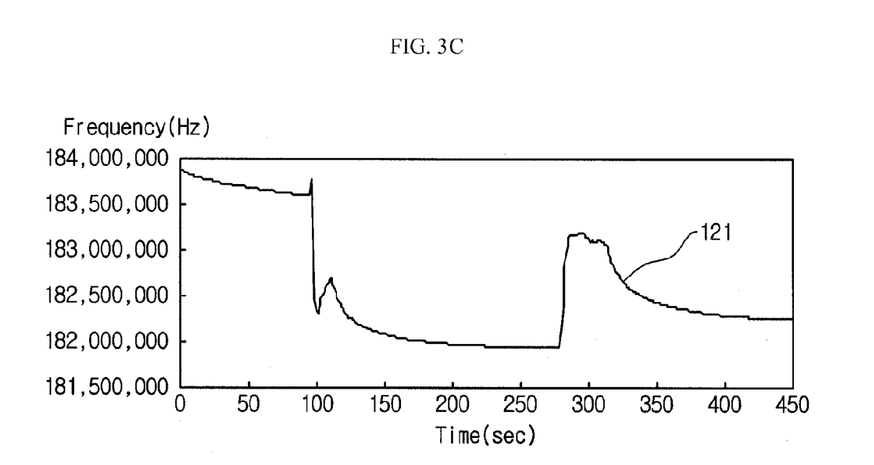
Figure 3D:
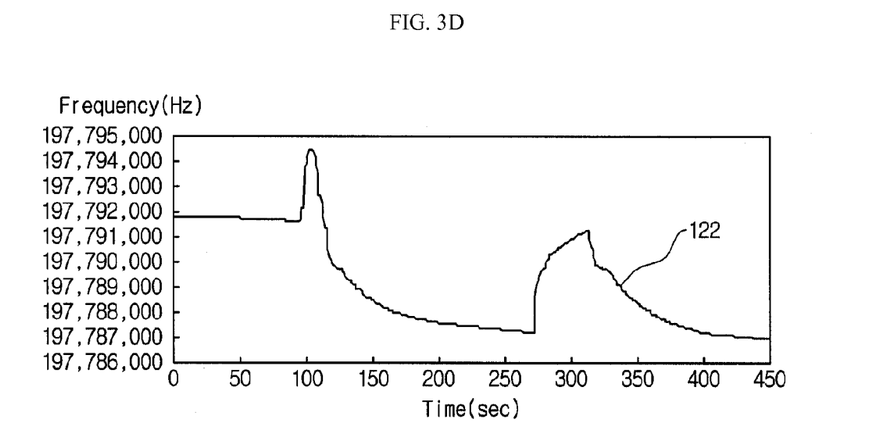

FIG. 3C and FIG. 3D are graphs of frequency (in Hz) versus time (in sec), which illustrate a frequency of an output signal of an exemplary embodiment of a SAW element and a frequency of an output signal of a SAW element according to the related art, as mass of the target material bound to the surface of the SAW element is changed. As shown, a change of a frequency of the output signal 121 of the exemplary embodiment of the SAW element is relatively larger than a change of a frequency of the output signal 122 of the SAW element according to the related art. In FIG. 3C, a concentration of a target material is increased from 0 to 1 ug/ml at the 90 second time resulting in a drop in frequency. A washing step that removed the target material from the SAW element was performed at the 280 second time.

The exemplary embodiments of a SAW element may provide an improved sensitivity for varying pressure and conductivity of a sample and mass of the target material, as compared to the SAW element according to the related art. The improved sensitivity occurs, in the exemplary embodiments of the SAW element because a portion of the SAW element where the SAW is propagated is relatively close to the sample being analyzed, since there is no need to form an additional insulation film on an entire surface of the SAW element.

Figure 4:
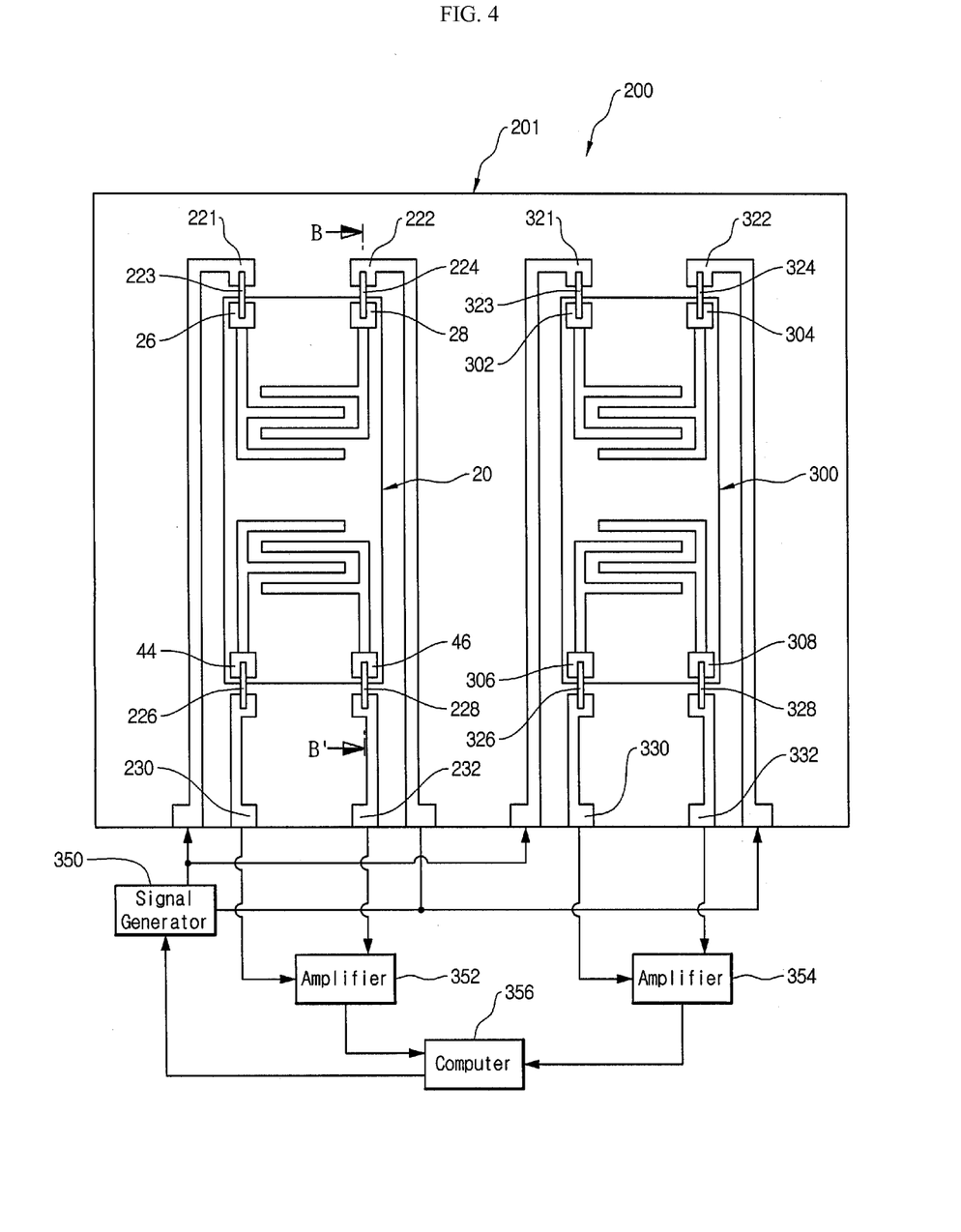
FIG. 4 is a top plan view illustrating an exemplary embodiment of a SAW device having an active SAW element and a reference SAW element.
Figure 5:
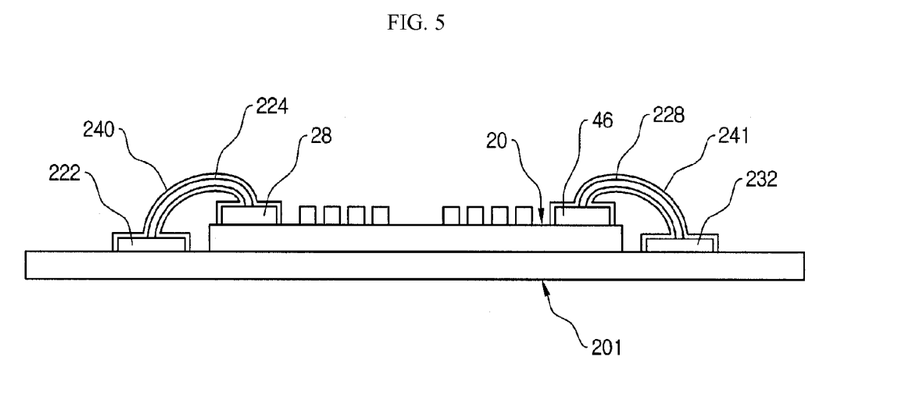
FIG. 5 is a cross-sectional view taken along line B-B' of FIG. 4.

FIG. 4 is a top plan view illustrating an exemplary embodiment of a SAW device 200, and FIG. 5 is a cross-sectional view taken along line B-B' of FIG. 4.

Referring to FIG. 4 and FIG. 5, the SAW device 200 may include a SAW element 20, a substrate 201, pad portions 221, 222, connecting portions 223, 224, 226, 228, pad portions 230, 232, oxide films 240, 242, a SAW element 300, pad portions 302, 304, 306, 308, 321, 322, connecting portions 323, 324, and pad portions 330, 332, a signal generator 350, and amplifiers 352, 354.

In FIG. 4 and FIG. 5, the SAW element 20 may be the SAW element 20 described in FIG. 1 and FIG. 2. However, the SAW element 20 included in the SAW device 200 is not restricted to the one illustrated in FIG. 1 and FIG. 2. For example, in an alternative exemplary embodiment, the SAW element 20 may be constructed differently from that illustrated in FIG. 1 and FIG. 2.

The substrate 201 may be a base substrate supporting some of the other components of the SAW device 200. The SAW element 20 and the SAW element 300 may be formed on the substrate 201 and may be disposed proximate to one another.

The SAW element 20 may have the pad portions 26, 28, 44, 46 that are provided for electrically coupling the SAW element 20 to external devices. The pad portions 26, 28, 44, 46 may be made of an electrically conducting, surface-oxidizable material. For example, the pad portions 26, 28, 44, 46 may be formed of any metal, including Al, Nb, Ta, Ti, W, Zr, Cu and Cr or alloys thereof, and may be formed of one or more of the metals.

Referring to FIG. 1 and FIG. 2, the pad portions 26, 28 of the SAW element 20 may correspond to portions of the electrodes 60, 62, 64, 66 and the pad portions 44, 46 may correspond to portions of the electrodes 70, 72, 74, 76 of the SAW element 20. In particular, the pad portions 26, 28 may be electrically coupled through the connecting portions 223, 224, respectively, to the pad portions 221, 222, respectively. The pad portions 221, 222 may be further electrically coupled to an external device such as the signal generator 350. Further, the pad portions 44, 46 may be electrically coupled through the connecting portions 226, 228, respectively, to the pad portions 230, 232, respectively. The pad portions 230, 232 may be further electrically connected to an external device such as the amplifier 352.

Referring to FIG. 4 and FIG. 5, the connecting portions 223, 224, 226, 228 may be constructed of an electrically conducting, surface-oxidizable material. For example, the connecting portions 223, 224, 226, 228 may be formed of any metal, including Al, Nb, Ta, Ti, W, Zr, Cu and Cr or alloys thereof, and may be formed of one or more of the metals.

Oxide films may be formed on the pad portions 26, 28, 44, 46 and the connecting portions 223, 224, 226, 228 to enclose them. For example, the oxide films 224, 228 may be formed by oxidizing a material of the pad portions 28, 46 and the connecting portions 224, 228. Since the pad portions 26, 28, 44, 46 and the connecting portions 223, 224, 226, 228 are insulated by the oxide films, it is possible to prevent a leakage current from flowing from the pad portions 26, 28, 44, 46 and the connecting portions 223, 224, 226, 228. In one exemplary embodiment, the oxide films may have a thickness greater than 10 nanometers. In another exemplary embodiment, the oxide films may have a thickness greater than 11 nanometers.

Figure 6:
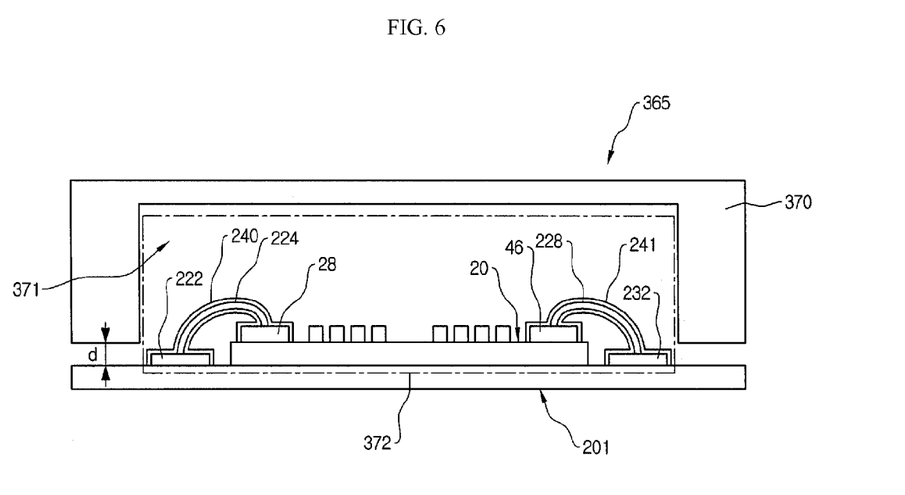
FIG. 6 is a cross-sectional view illustrating another alternative exemplary embodiment of a SAW device.

In an exemplary embodiment, referring to FIG. 4 and FIG. 6, the oxide films on the pad portions 26, 28, 44, 46 and the connecting portions 223, 224, 226, 228 may be formed by dry oxidation. For example, the oxide films may be formed by exposing the pad portions 26, 28, 44, 46 and the connecting portions 223, 244, 226, 228 to a plasma. For example, an oxygen plasma may be utilized to form the oxide films 240, 241 on the pad portions 28, 46 and the connecting portions 224, 228. Alternatively, for example, the oxide films 240, 241 may be formed by thermally oxidizing the pad portions 28, 46 and the connecting portions 224, 228, or via an ozone cleaning process.

In another exemplary embodiment, oxide films on the pad portions 26, 28, 44, 46 and the connecting portions 223, 224, 226, 228 may be formed by wet oxidization. For example, the oxide films 240, 241 may be formed by exposing the pad portions 28, 46 and the connecting portions 224, 228 to at least one of H2O2, NaHCO3, PbO2, MnO2, KMnO4, NaClO, and Cl2O.

Alternatively, the oxide films 4 on the pad portions 26, 28, 44, 46 and the connecting portions 223, 224, 226, 228 may be formed by anodizing each of the pad portions 26, 28, 44, 46 and the connecting portions 223, 224, 226, 228. During the anodizing process, a solution containing sulfuric acid, oxalic acid, chromic acid, boric acid, borax, ammonium phosphate or ammonium tartrate may be used as an electrolyte solution.

Referring to FIG. 4, the SAW element 300 may have a substantially similar structure as the SAW element 20, except that the SAW element 300 does not have the receptors 48 which bind to a target material. In particular, the pad portions 302, 304, 306, 308 may have a substantially similar structure as the pad portions 26, 28, 44, 46, respectively. Further, the pad portions 321, 322, 330, 332 may have a substantially similar structure as the pad portions, 221, 222, 230, 232, respectively. Further, the connecting portions 323, 324, 326, 328 may have a substantially similar structure as the connecting portions 223, 224, 226, 228, respectively.

The signal generator 350 may be electrically coupled to the pad portions 221, 222 that may be further electrically coupled through the connecting portions 223, 224 to the pad portions 26, 28 of the SAW element 20. The signal generator 350 may be further electrically coupled to the pad portions 321, 322 that may be further electrically coupled through the connecting portions 323, 324 to the pad portions 302, 304 of the SAW element 300. The signal generator 350 may supply an electrical signal (e.g., an oscillatory electrical signal) to both the SAW element 20 and the SAW element 300 in response to a control signal from the computer 356 to induce the SAW elements 20, 300 to generate first and second SAW waves, respectively, therein.

The amplifier 352 may be electrically coupled to the pad portions 230, 232 of the SAW element 20. The amplifier 352 may amplify a signal received from the SAW element 20 indicative of an amount of target material or a concentration of target material bonded to the SAW element 20.

The amplifier 354 may be electrically coupled to the pad portions 330, 332 of the SAW element 300. The amplifier 354 may amplify a reference signal received from the SAW element 300.

The computer 356 may be electrically coupled to the signal generator 350 and the amplifiers 352, 354. The computer 356 may generate a control signal to induce the signal generator to output a signal (e.g., an oscillatory electrical signal) that is received by the SAW elements 20, 300. The SAW elements 20, 300 may generate first and second SAW waves, also known as mechanical waves, in response to the control signal. The SAW elements 20, 300 may output first and second output signals, respectively, which are amplified by amplifiers 352, 354, respectively. The computer 356 may receive the first and second output signals (either amplified, or non-amplified if the amplifiers 352, 354 are not utilized) to determine an amount of a target material or a concentration of the target material based on the first and second output signals. Further the computer 356 may store a target material amount value or a target material concentration value in an internal memory device or an external memory device. In one exemplary embodiment, the computer 356 may utilize a frequency shift between the first and second output signals to determine an amount or concentration of a detected target material. In particular, when a mass change occurs due to a target material bonding to the active SAW element 20, a difference in a center frequency of the first and second output signals increases with an increasing amount of target material being bonded to the active SAW element 20. In another exemplary embodiment, the computer 356 may utilize a phase shift between the first and second output signals to determine an amount or concentration of a detected target material. In another exemplary embodiment, the computer 356 may utilize an amplitude change between the first and second output signals to determine an amount or concentration of a detected target material.

The SAW device 200 may be exposed to a sample including a target material. At this time, the target material in the sample may be bound to the SAW element 20. When the target material is bound to the SAW element 20, a characteristic of the SAW generated by the SAW element 20 may be changed as discussed above.

Further, the SAW device 200 may include a plurality of SAW elements. One SAW element of the plurality of SAW elements may be bound to the target material to measure the target material and the other SAW element(s) may not be bound to the target material so as to be used as a reference element. By comparing an output signal of the SAW element combined with the target material with an output signal of the reference element, it is possible to analyze the target material quantitatively and qualitatively.

In the SAW device 200 shown in FIG. 4 and FIG. 5, oxide films 4 may be formed on the pad portions 26, 28, 44, 46 and the connecting portions 223, 224, 226, 228. Accordingly, even when the pad portions 26, 28, 44, 46 and the connecting portions 223, 224, 226, 228 are exposed to a conductive liquid sample, it is possible to prevent a leakage current from flowing through the sample.

Further, since an additional insulating film is not needed on the pad portions 26, 28, 44, 46 and the connecting portions 223, 224, 226, 228, a manufacturing process for manufacturing a SAW device may be simplified. Further, it is possible to reduce a size of the SAW device and prevent contamination caused by a reagent or the like in a patterning process.

FIG. 6 is a cross-sectional view illustrating another exemplary embodiment of a SAW device 365. The SAW device 365 may include a chamber 372 formed adjacent to the SAW elements 20, 300 to cover the SAW elements 20, 300.

In FIG. 6, a structure and a functionality of the SAW elements 20, 300 and the substrate 201 in the SAW device 365 are the same as the embodiment described above in FIG. 4 and FIG. 5. Therefore, a detailed description thereof will be omitted for the purpose of brevity.

Further, the SAW device 365 may include a structure 370 facing the substrate 201 and disposed above the substrate 201. The structure 370 may form a chamber or space 372 which is positioned adjacent to the SAW element 20 for collecting a sample therein. The structure 370 may be formed of a material appropriate to form the chamber 372. The material utilized to form the structure 370 may be a polymer, for example.

A bottom portion of the structure 370 may include a concave portion 371. The concave portion 371 of the structure 370 may be positioned adjacent to the SAW elements 20, 300. Accordingly, the chamber 372 may have a volume larger than a volume of the SAW elements 20, 300.

As shown in FIG. 6, the substrate 201 and the structure 370 may be positioned apart from each other by a predetermined gap d wherein the chamber 372 of the structure 370 is disposed proximate to the substrate 201. However, in an exemplary embodiment, the substrate 201 and the structure 370 may be connected to each other in an area other than the chamber 372. Further, the structure 370 may further include a concave portion (not shown) which forms a channel through which a sample with a target material may flow into the chamber 372, in addition to the concave portion 371.

Figure 7:
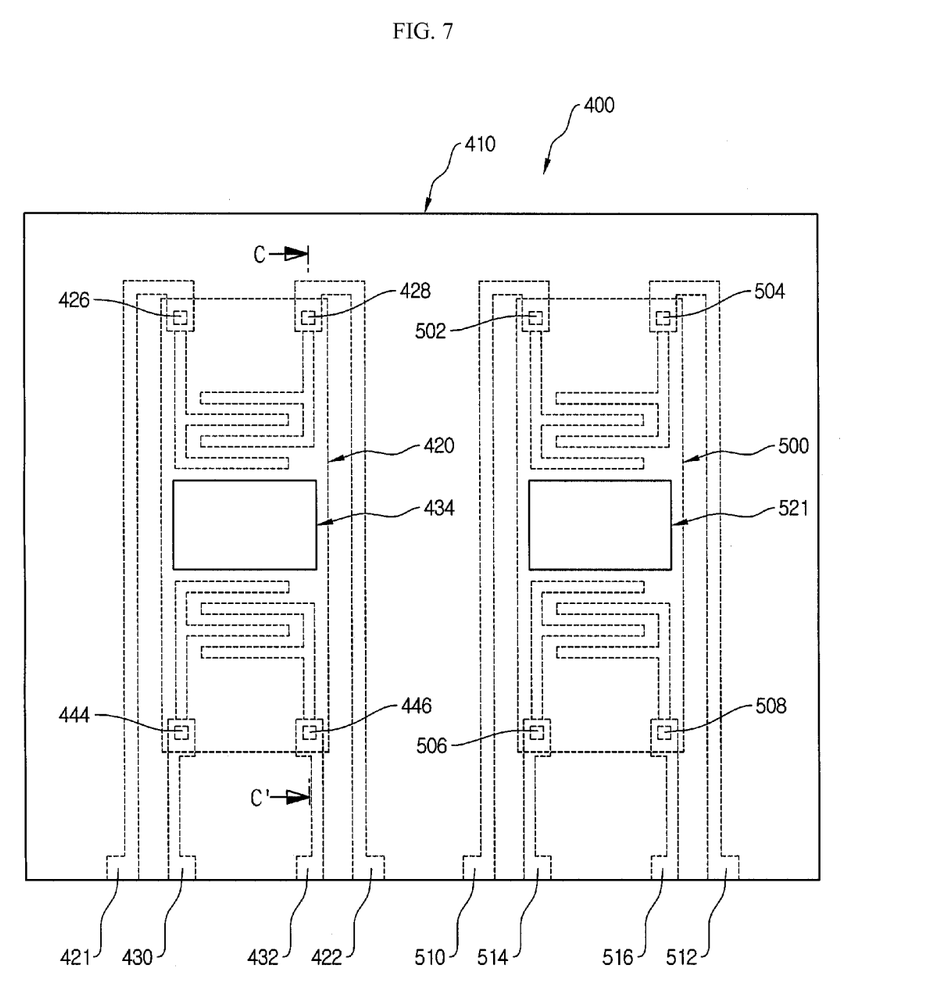
FIG. 7 is a top plan view illustrating another alternative exemplary embodiment of a SAW device.
Figure 8:
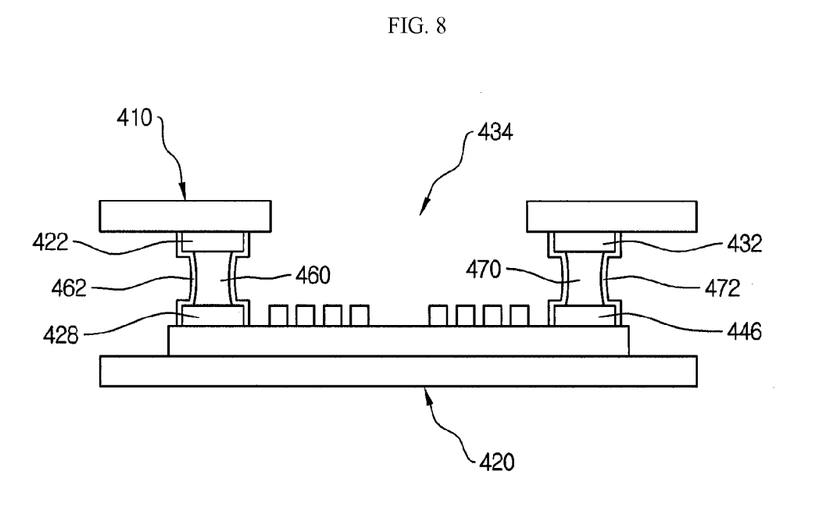
FIG. 8 is a cross-sectional view taken along line C-C' of FIG. 7.

FIG. 7 is a top plan view illustrating another exemplary embodiment of a SAW device 400, and FIG. 8 is a cross-sectional view taken along line C-C' of FIG. 7.

Referring to FIG. 7, the SAW device 400 may include a substrate 410, a SAW element 400, pad portions 421, 422, 430, 432, a SAW element 500 and pad portions 510, 512, 514, 516. The SAW element 400 has pad portions 426, 428, 444, 446 and the SAW element 500 has the pad portions 502, 504, 506, 508. Since a structure and a functionality of the SAW elements 420, 500 are substantially similar to SAW elements 20, 300 in FIG. 4 and FIG. 5, a detailed description thereof will be omitted for the purpose of brevity.

The substrate 410 may include one or more holes 434 formed in a portion of the substrate 410. The SAW element 420 may be exposed through the holes 434 of the substrate 410. When the substrate 410 having the holes 434 formed thereon is exposed to the sample, the SAW element 420 positioned below the substrate 410 may be exposed to the sample through the holes 434. For example, a portion of the substrate 410 where a receptor 48 (exemplary receptors shown in FIG. 1 on SAW element 12) is disposed thereon may communicate via the hole 434 with the sample. Alternatively, in an exemplary embodiment, the SAW device 400 may further include a cover (not shown) positioned on the substrate 410 to cover the holes 434. Further, the substrate 410 may include one or more holes 521 formed in a portion of the substrate 410. The SAW element 500 may be exposed through the holes 521 of the substrate 410.

Since the substrate 410 has the holes 434 formed therein, the SAW element 420 may be exposed to the sample positioned in the holes 434. Thus, the holes 434 themselves may serve as a chamber to collect the sample. The depth and size of the holes 434 may be appropriately controlled according to a desired exposure level of the sample to the SAW element 420.

Referring to FIG. 8, the pad portions 428, 422 may be electrically connected to each other by a connecting portion 460 having a bump shape. A bump shape may refer to a curved shape or a polyhedron shape. For example, the connecting portion 460 may be formed of a metal having a curved shape or a polyhedron shape.

Figure 9A:
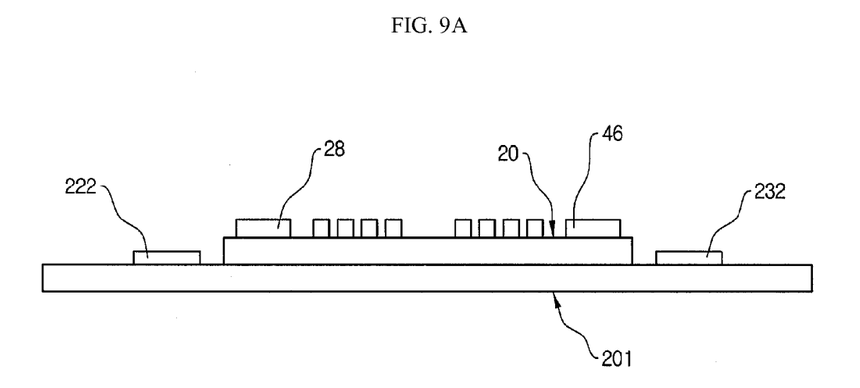
FIGS. 9A-9C are cross-sectional views illustrating an exemplary embodiment of a method for manufacturing a SAW device.
Figure 9B:
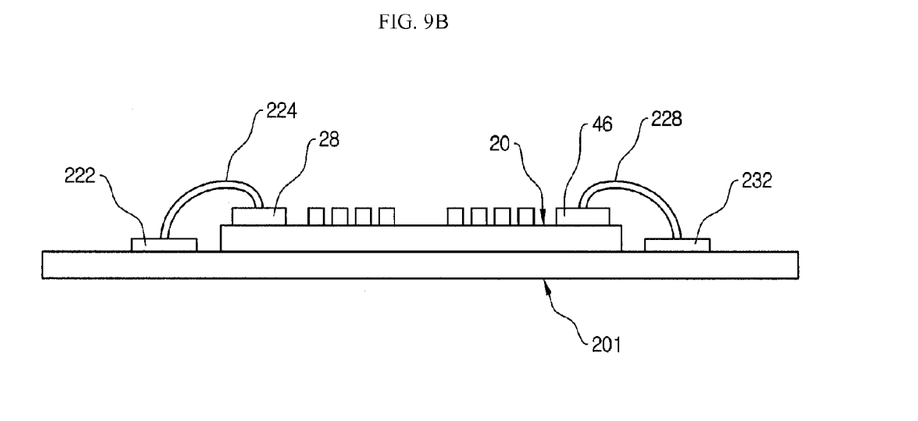
Figure 9C:
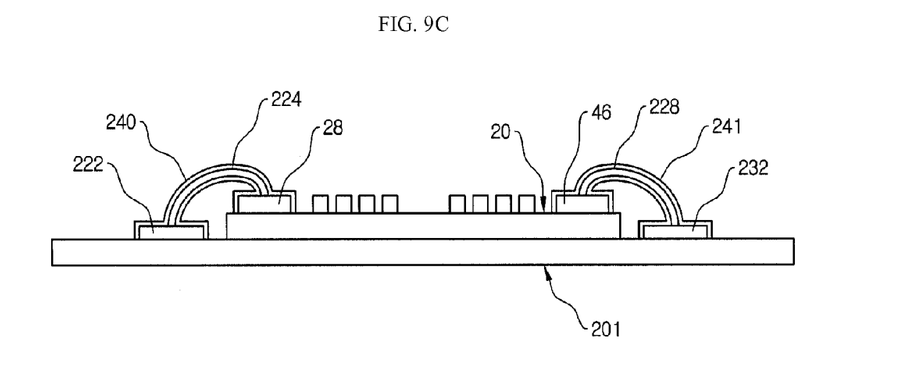

In an exemplary embodiment, the connecting portion 460 may be used not only to electrically connect the pad portions 428, 422, but also to bond the SAW element 420 to the substrate 410. For example, the connecting portion 460 constructed of metal may be used to connect to the pad portions 428, 422. Alternatively, the connecting portion 460 may include a solder ball, and the pad portions 428, 422 may be connected to each other via the connecting portion 460. FIGS. 9A-9C are cross-sectional views illustrating an exemplary embodiment of a method for manufacturing the SAW element 10. For purposes of simplicity, only a portion of the components of the SAW element 10 will be discussed in detail below.

Referring to FIG. 9A, the SAW element 10 including the pad portions 28, 46, the pad portions 222, 232, and the substrate 201 may be provided. For purposes of simplicity, the remaining pad portions of the SAW element 10 will not be discussed below.

While a structure and an arrangement of the SAW element 10 and the substrate 201 in the exemplary embodiment of FIG. 9A are illustrated in a similar manner as shown in the exemplary embodiment of FIG. 1 and FIG. 5, the embodiment of FIG. 9A is only an example. Alternatively, the SAW element 10 and the substrate 201 may be constructed as shown in FIG. 7 or may have a different structure and arrangement.

That is, although the SAW element 10 may be positioned on the substrate 201 in FIG. 9A, the SAW element 10 may also be disposed apart from the substrate 201 according to another exemplary embodiment. For example, the SAW element 10 may be disposed apart from the substrate 201 and be positioned above or below the substrate 201.

The SAW element 10 may include the pad portions 28, 46, and the substrate 201 may include the pad portions 222, 232. The pad portions 28, 46 may transfer electrical signals, and may be constructed of an electrically conducting, surface-oxidizable material. For example, each of the pad portions 28, 46 may be formed of any metal including Al, Nb, Ta, Ti, W, Zr, Cu and Cr or alloys thereof, and may be formed of one or more of the metals.

Referring to FIG. 9B, the pad portions 222, 28 may be electrically connected to each other via the connecting portion 224. Further, the pad portions 46, 232 may be electrically connected to each other via the connecting portion 228. Accordingly, the connecting portions 224, 228 may be made of an electrically conducting, surface-oxidizable material. For example, the connecting portions 224, 228 may be formed of any metal including Al, Nb, Ta, Ti, W, Zr, Cu and Cr or alloys thereof, and may be formed of one or more of the metals.

Although the connecting portions 224, 228 each have a shape of a line in FIG. 9B, the connecting portions 224, 228 are only examples and the connecting portions 224, 229 may have any predetermined shape which is appropriate for an electrical connection. For example, the connecting portions 224, 228 may have a curved shaped or a polyhedron shape. Further, the connecting portions 224, 228 may include a metal or solder ball.

Referring to FIG. 9C, the oxide film 240 may be formed on the pad portions 222, 28 and the connecting portion 224. The oxide film 240 may completely enclose the pad portions 222, 28 and the connecting portion 224. Further, the oxide film 241 may be formed on the pad portions 46, 232 and the connecting portion 228. The oxide film 241 may completely enclose the pad portions 46, 232 and the connecting portion 228.

In an exemplary embodiment, the oxide films 240, 241 may be formed by dry oxidation. For example, the oxide film 240 may be formed by exposing each of the pad portions 222, 28 and the connecting portion 224 to a plasma. Further, for example, the oxide film 241 may be formed by exposing each of the pad portions 46, 232 and the connecting portion 228 to a plasma. In particular, oxygen plasma may be utilized to form the oxide films 240, 241. Further, the oxide films 240, 241 may be formed by thermally oxidizing each of the associated pad portions and associated connecting portions or via an ozone cleaning process.

Further, the oxide films 240, 241 may be formed by wet oxidation. For example, the oxide film 240 may be formed by exposing the pad portions 222, 28 and the connecting portion 224 to hydrogen peroxide. Further, for example, the oxide film 241 may be formed by exposing the pad portions 46, 232 and the connecting portion 228 to hydrogen peroxide. Alternatively, the oxide films 240, 241 may be formed by exposing each of the associated pad portions and the associated connecting portion to an oxidizing agent such as NaHCO3, PbO2, MnO2, KMnO4, NaClO or Cl2O.

Alternatively, the oxide film 240 may be formed by anodizing the pad portions 222, 28 and the connecting portion 224. For example, the oxide film 240 may be formed by exposing the pad portions 222, 28 and the connecting portion 224 to an electrolyte solution and applying electrical power to the pad portions 222, 28 and the connecting portion 224. Further, the oxide film 241 may be formed by anodizing the pad portions 46, 232 and the connecting portion 228. The thickness of the oxide films 240, 241 may be determined based on a temperature of the electrolyte solution, a magnitude of the applied electrical power, a time period of application, and other related variables.

For example, when the pad portions 222, 28 and the connecting portion 224 are formed of aluminum (Al), the oxide film 240 may be formed by applying a voltage of about 100 Volts for about 30 minutes in an aqueous solution of ammonium tartrate of about 20° C. having a concentration of about 0.16 M. The electrolyte solution may contain sulfuric acid, oxalic acid, chromic acid, boric acid, borax, ammonium adipate or phosphate. The oxide film 241 may be formed on the pad portions 46, 232 and the connecting portion 228 in a similar manner.

By forming the oxide films 240, 241, the pad portions 222, 28 and the connecting portion 224 may be electrically insulated by the oxide film 240, and the pad portions 46, 232 and the connecting portion 228 may be electrically insulated by the oxide film 241, even when the SAW element 20 or the SAW device 10 including the SAW element 20 is exposed to a liquid sample. Accordingly, even when a conductive liquid sample or the like is used, it is possible to prevent a leakage current from flowing from the pad portions 222, 28, 46, 232 and the connecting portions 224, 228 through the sample.

The present disclosure should not be construed as being limited to the exemplary embodiments set forth herein. Rather, these exemplary embodiments are provided so that this disclosure will be thorough and complete and will fully convey the concept of the exemplary embodiments to those skilled in the art.

Further, although the exemplary embodiments have been shown and described herein, it will be understood by those of ordinary skill in the art that various changes and modifications in form and details may be made therein without departing from the spirit or scope of the claimed invention as defined by the following claims.

What is claimed is:

1. A surface acoustic wave element for analyzing a biological material, comprising:
   a first substrate comprising a piezoelectric material including a pad portion;
   a second substrate including another pad portion; at least one connecting portion which electrically connects respective pad portions on the first and second substrates;
   a first electrode disposed on the first substrate;
   a second electrode disposed on the first substrate;
   first and second oxide films disposed on the first and second electrodes; and
   a receptor disposed on the first substrate on a portion of the substrate between the first electrode and the second electrode, the receptor configured to bind to a target material that contacts the receptor,
   wherein the first and second electrodes are constructed integrally with a respective pad portion, and
   wherein the first and second oxide films are disposed on the first and second electrodes excluding an area of the pad portion.

2. The surface acoustic wave element according to claim 1, wherein the first electrode comprises a surface-oxidizable conductive material.

3. The surface acoustic wave element according to claim 2, wherein the surface-oxidizable conductive material is at least one of a metal and an alloy.

4. The surface acoustic wave element according to claim 3, wherein the surface-oxidizable conductive material comprises at least one of aluminum, niobium, tantalum, titanium, tungsten, zirconium, copper and chromium.

5. The surface acoustic wave element according to claim 1, wherein the first electrode is an interdigital transducer electrode.

6. The surface acoustic wave element of claim 1, wherein the first and second oxide films are disposed on the first and second electrodes, respectively, by wet oxidation of the first and second electrodes, respectively, utilizing an oxidizing agent.

7. A surface acoustic wave device, comprising:
   a surface acoustic wave element including a first pad portion;
   a first substrate including a second pad portion;
   a connecting portion which electrically connects the first pad portion and the second pad portion; and
   an oxide film which is disposed on the first pad portion, the second pad portion and the connecting portion;
   the surface acoustic wave element further comprises:
   a second substrate comprising a piezoelectric material;
   a plurality of first electrodes which are disposed on the second substrate and are separated from each other;
   a plurality of second electrodes which are disposed on the second substrate and are separated from the first electrodes and are separated from each other; and
   oxide films which are disposed on the respective plurality of first electrodes and plurality of second electrodes,
   wherein the first pad portion is constructed integrally with the plurality of first electrodes and the plurality of second electrodes.

8. The surface acoustic wave device according to claim 7, wherein the first pad portion comprises a surface-oxidizable conductive material.

9. The surface acoustic wave device according to claim 8, wherein the surface-oxidizable conductive material is a metal or an alloy.

10. The surface acoustic wave device according to claim 9, wherein the surface-oxidizable conductive material comprises at least one of aluminum, niobium, tantalum, titanium, tungsten, zirconium, copper and chromium.

11. A surface acoustic wave element for analyzing a biological material, comprising:
    a first substrate comprising a piezoelectric material including a pad portion;
    a second substrate including another pad portion; a connecting portion which electrically connects respective pad portions on the first and second substrates;
    at least one electrode disposed on the first substrate having an oxide film formed on the at least one electrode; and
    at least one receptor disposed on the substrate on a portion of the first substrate,
    wherein the at least one receptor is constructed to react with a target material,
    wherein the target material is included in a conductive sample,
    wherein the oxide film is adapted to prevent a current leakage through the conductive sample,
    wherein the at least one electrode is constructed integrally with a respective pad portion, and
    wherein the oxide film is disposed on the at least one electrode excluding an area of the pad portion.

12. The surface acoustic wave element of claim 11, wherein oxide film prevents a leakage current from flowing from the electrode to the liquid.

13. The surface acoustic wave element of claim 1, wherein the oxide film is formed on the connecting portion by oxidation.

14. The surface acoustic wave element according to claim 1, wherein the piezoelectric material is a lithium tantalite, a lithium niobate, or a piezoelectric ceramic.

15. The surface acoustic wave element according to claim 6, wherein the oxidizing agent is sodium bicarbonate, lead dioxide, manganese dioxide, potassium permanganate, sodium hypochlorite, or chlorine oxide.

16. The surface acoustic wave element according to claim 6, wherein the wet oxidation is conducted by anodizing the electrode.

17. The surface acoustic wave element according to claim 1, wherein the pad portion is electrically coupled to external signal generator or external amplifier.

18. The surface acoustic wave element according to claim 1, wherein the connecting portion comprises a surface-oxidizable conductive material.

19. The surface acoustic wave element according to claim 18, wherein the surface-oxidizable conductive material is at least one of a metal and an alloy.

20. The surface acoustic wave element according to claim 18, wherein the surface-oxidizable conductive material comprises at least one of aluminum, niobium, tantalum, titanium, tungsten, zirconium, copper, chromium and an alloy.

21. The surface acoustic wave element according to claim 1, wherein an oxide film is formed on each of the connecting portion by oxidation.

22. The surface acoustic wave device according to claim 7, wherein the connecting portion comprises a surface-oxidizable conductive material.

23. The surface acoustic wave element according to claim 11, wherein the piezoelectric material is a lithium tantalite, a lithium niobate, or a piezoelectric ceramic.

24. The surface acoustic wave element of claim 11, wherein the oxide film is formed on each of the at least one electrode by dry oxidation.

25. The surface acoustic wave element according to claim 24, wherein the dry oxidation is conducted by exposing the electrode to a plasma, thermally oxidizing the electrode, or an ozone cleaning process.

26. The surface acoustic wave element according to claim 11, wherein an output signal generated from at least one electrode upon the binding of the target material with the receptors indicates an amount or concentration of the target material.

27. The surface acoustic wave element according to claim 11, wherein an output signal generated from at least one electrode upon the binding of the target material with the receptors indicates the presence of the target material.

28. A surface acoustic wave device comprising,
a first substrate comprising a piezoelectric material including a pad portion;
a second substrate including another pad portion; at least one connecting portion which electrically connects respective pad portions on the first and second substrates;
at least one interdigital transducer electrode disposed on the first substrate; and
at least one receptor disposed directly on the first substrate on an exposed portion of the substrate,
wherein a target material in a liquid sample binds to the receptor,
wherein a difference between input and output signals generated from at least one interdigital transducer electrode upon the binding of target material with the receptors indicates the presence, amount or concentration of the target material;
wherein an oxide film is formed on each of the interdigital transducer electrode by oxidation;
wherein the at least one interdigital transducer electrode is constructed integrally with a respective pad portion; and
wherein the oxide film is formed on the interdigital transducer electrode excluding an area of the pad portion.

29. The surface acoustic wave element according to claim 28, wherein the oxidation is a dry oxidation or a wet oxidation.

30. A surface acoustic wave element, comprising:
a first substrate comprising a piezoelectric material including a pad portion;
a second substrate including another pad portion; at least one connecting portion which electrically connects respective pad portions on the first and second substrates;
a plurality of first surface-oxidizable electrodes which are disposed on the first substrate;
a plurality of second surface-oxidizable electrodes which are disposed on the first substrate and are separated from the first surface-oxidizable electrodes;
a first oxide film which is formed directly on the plurality of first surface-oxidizable electrodes by oxidation of the plurality of first surface-oxidizable electrodes;
a second oxide film which is formed directly on the plurality of second surface-oxidizable electrodes by oxidation of the plurality of second surface-oxidizable electrodes; and
at least one receptor disposed on the first substrate on a portion of the first substrate between the plurality of first surface-oxidizable electrodes and the plurality of second surface-oxidizable electrodes,
wherein the plurality of first and second surface-oxidizable electrodes are constructed integrally with a respective pad portion, and
wherein the first and second oxide films are disposed on the plurality of first and second surface-oxidizable electrodes excluding an area of the pad portion.

* * * * *